United States Patent
Glushkov et al.

(10) Patent No.: US 8,569,489 B2
(45) Date of Patent: Oct. 29, 2013

(54) 7-[4-(BENZHYDRYLPIPERAZINYL-1)BUTYL]-3-METHYLXANTHINE AND ITS SALTS WITH ORGANIC OR INORGANIC ACIDS POSSESSING ANTIHISTAMINIC AND ANTIALLERGENIC ACTIVITY

(75) Inventors: Robert G. Glushkov, Moscow (RU); Sergei D. Juzhakov, Moscow (RU); Olga S. Fominova, Moscow (RU); Nelli M. Sazonova, Yubileiny (RU); Elena M. Dolginova, Moscow (RU); Vadim A. Shorr, Moscow (RU); Mikhail V. Borovkov, Moscow (RU); Valentina V. Asnina, Moscow (RU)

(73) Assignee: A.B. Intelpharm Limited, Nicosia (CY)

( * ) Notice: Subject to any disclaimer, the term of this patent is extended or adjusted under 35 U.S.C. 154(b) by 731 days.

(21) Appl. No.: 12/568,880

(22) Filed: Sep. 29, 2009

(65) Prior Publication Data
US 2010/0168425 A1 Jul. 1, 2010

Related U.S. Application Data

(63) Continuation of application No. PCT/RU2008/000166, filed on Mar. 20, 2008.

(30) Foreign Application Priority Data

Mar. 29, 2007 (RU) ................................. 2007111380
Mar. 17, 2008 (RU) ................................. 2008109708

(51) Int. Cl.
*C07D 473/04* (2006.01)
*A61P 37/08* (2006.01)

(52) U.S. Cl.
USPC ......................................................... 544/272

(58) Field of Classification Search
USPC ......................................................... 544/272
See application file for complete search history.

(56) References Cited

U.S. PATENT DOCUMENTS

| 4,361,565 | A | * | 11/1982 | Temple et al. ............ 514/253.12 |
|---|---|---|---|---|
| 4,423,049 | A | * | 12/1983 | Temple, Jr. ............... 514/252.18 |
| 4,524,206 | A | * | 6/1985 | New et al. ...................... 544/230 |
| 4,543,254 | A |  | 9/1985 | Kaneko et al. |
| 4,548,820 | A |  | 10/1985 | Regnier et al. |
| 4,564,617 | A | * | 1/1986 | Sugimoto et al. ......... 514/263.22 |
| 4,668,786 | A | * | 5/1987 | Thiele et al. .................... 544/267 |
| 4,716,165 | A |  | 12/1987 | Abou-Gharbia et al. |
| 4,737,500 | A | * | 4/1988 | Sorg .............................. 514/222.8 |
| 4,933,453 | A | * | 6/1990 | Hrib et al. ....................... 544/297 |
| 7,432,269 | B2 | * | 10/2008 | Capet et al. ............... 514/253.01 |

FOREIGN PATENT DOCUMENTS

| GB | 2107709 A | * | 5/1983 |
|---|---|---|---|
| JP | 58148828 A |  | 9/1983 |
| WO | 2001079188 A1 |  | 10/2001 |

OTHER PUBLICATIONS

Suzuki, Chem Pharm Bull vol. 47;1322-1325(1999).*
Dridi, D. et al., "Circadian Time-Dependent Differences in Murine Tolerance to the Antihistaminic Agent Loratadine," Chronobiology International, vol. 22, No. 3, 2005, pp. 499-514.
Kochergin, P.M. et al., "Chemistry of Heterocyclic Compounds (CHC)," KhGS, No. 9, 1995, pp. 388-390.
Mashkovsky, M.D., "Lekarstvennye Sredstva [Drugs]," 15th Edition, Moscow, 2005, pp. 272-283.
Pascal, J.-C. et al., "New Antihistaminic Theophylline or Theobromine Derivatives," Journal of Medicinal Chemistry, vol. 28, No. 5, 1985, pp. 647-652.
Roth, H.J., "Reaction of Theophylline and Theobromine with 1,2-epoxides," Arch. Pharm., vol. 292, 1959, pp. 234-238.
Rubtsov, M.V. et al., "Sinteticheskiye khimiko-farmatsevticheskiye preparaty [Synthetic chemical and pharmaceutical preparations]," Meditsina, Moscow, 1971, pp. 288-289.
Zechel, H.-J. et al., "Pharmacological and Toxicological Properties of Azelastine, a Novel Antiallergic Agent," Arzneimittel-Forschung/Drug Research, vol. 31, No. 8, 1981, pp. 1184-1193.
International Search Report, mailed Jul. 10, 2008, from International Application No. PCT/RU2008/000166, filed Mar. 20, 2008.

* cited by examiner

*Primary Examiner* — Kortney L Klinkel
*Assistant Examiner* — John Mauro
(74) *Attorney, Agent, or Firm* — Patentbar International, P.C.

(57) ABSTRACT

The invention relates to a range of original xanthine derivatives substituted in 1 -and 7-positions with benzhydryl-4-piperazinyl-1-alkane fragments. A method for obtaining 3-methyl-7-[4-(benzhydryl-4-piperazinyl-1)butyl]xanthine and the salts thereof with organic and inorganic acids by alkylating the 7-potassium salt of 3-methylxanthine by 1,4-dibromobutane, by subsequently interacting the thus formed 7-(4-bromobutyl)-3-methylxanthine with 1-benzhydrylpiperazinyl and by neutralising the thus obtained radical 7-/4-(4-benzhydrylpiperazinyl-1) butyl/-3-methylxanthine by an organic or inorganic acid is also disclosed.

20 Claims, No Drawings

7-[4-(BENZHYDRYLPIPERAZINYL-1)BUTYL]-3-METHYLXANTHINE AND ITS SALTS WITH ORGANIC OR INORGANIC ACIDS POSSESSING ANTIHISTAMINIC AND ANTIALLERGENIC ACTIVITY

RELATED APPLICATIONS

This application is a Continuation of International Application No. PCT/RU2008/000166 filed Mar. 20, 2008, which claims priority to Russian Patent Application Nos. RU 2007111380 filed Mar. 29, 2007, and RU 2008109708 filed Mar. 17, 2008, all of which are incorporated herein by reference in their entirety.

BACKGROUND OF THE INVENTION

Despite a rather large formulary of antihistaminic drugs used in medical practice as antiallergic agents, the search for new H-1 histamine receptor blockers remains an urgent task, inasmuch as most existing preparations of this class have deficiencies, such as short duration of action, the presence of side effects on the central nervous system, and so forth. (M. D. Mashkovsky, *Lekarstvennye sredstva* [Medications], Moscow, Novaya volna, 2005, 15$^{th}$ edition, pp. 285-297). In this regard, the search for original antihistamine (antiallergic) medications with a novel chemical structure is of special interest, and, in particular, the xanthine derivatives series, among which are a number of highly active natural compounds (theophylline, theobromine, caffeine) with valuable pharmacotherapeutic properties.

SUMMARY OF THE INVENTION

The goal of this invention is to expand the list of antihistaminic (antiallergic) medications.

This goal is achieved by synthesis and evaluation of the biological activity of original chemical compounds based on the xanthine structure, in particular derivatives of the 1- and 7-[ω(benzhydryl-4-piperazinyl-1)alkyl]-3-alkylxanthines, including their racemates or optical isomers, as well as their pharmaceutically acceptable salts and/or hydrates, of the general formulae I and II:

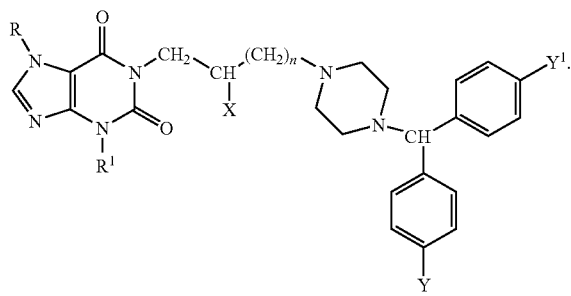

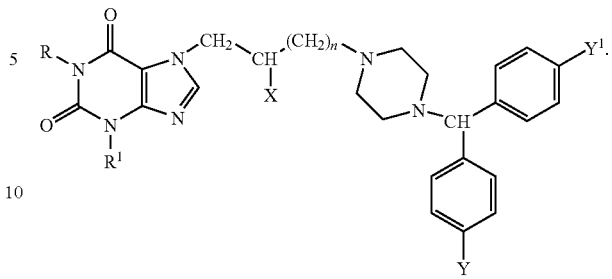

where R=H, Me, CH$_2$Ph; R$^1$=Me, n-C$_4$H$_9$; and n=0-3
X=H, OH, OCOCH$_2$CH$_2$COOH; Y and Y$^1$=H, Cl, F;
which have antihistaminic and antiallergic activity and can be used in medicine to prepare new highly active and low-toxicity antiallergic medications based on them.

The compounds on which a claim is made are synthesized using the following methods:

Method A.

Xanthine derivatives of general formulae III and IV, where R=H, Me, CH$_2$Ph; R$^1$=Me, and n-C$_4$H$_9$,

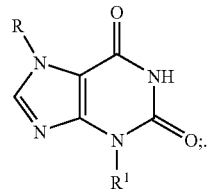

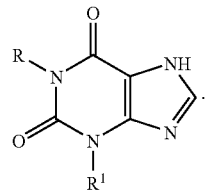

which are obtained using Traube's classical method (K. V. Vatsuro and G. L. Mishchenko, *Imennye reaktsii v organicheskoy khimii* [Named reactions in organic chemistry], Moscow, Khimiya, 1976, p. 400; P. M. Kochergin et al., *KhGS,* 1995, No. 9, p. 388) and are alkylated as a salt with an alkali metal (Na, K) by α,ω-dibromoalkanes of general formula V:

Br(CH$_2$)$_n$Br(V, where n=2-5).

The bromoalkylxanthines of general formulae VI and VII that are formed, where R=H, Me, CH$_2$Ph; R$^1$=CH$_3$, n-C$_4$H$_9$; and n=2-5,

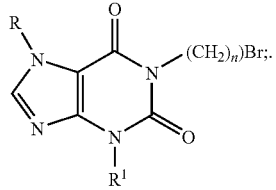

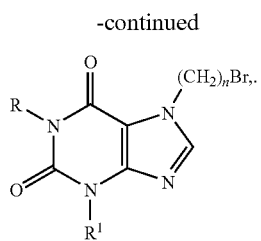

are treated in the presence of potassium iodide with substituted benzhydrylpiperazines of general formula VIII:

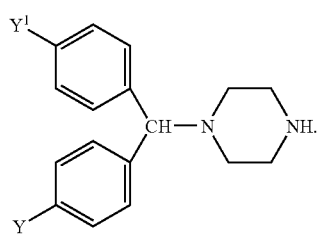

where Y and Y'=H, Cl, F.
therewith compounds I and II being claimed are derived, where X=H (Table 1).

Method B.

In accordance with this method, xanthine derivatives III and IV, where R=H, Me, CH$_2$Ph; R$_1$=Me, and n-C$_4$H$_9$ are treated with epichlorhydrin. Depending on the conditions of the reaction (nonaqueous or aqueous medium), the 1- or 7-(2,3-epoxy-propyl) (IX and X, where

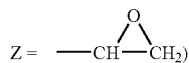

or 1- and 7-(3-chlor-2-hydroxypropyl) substituted xanthines (IX and X, where Z=—CH(OH)—CH$_2$Cl) are formed in the process.

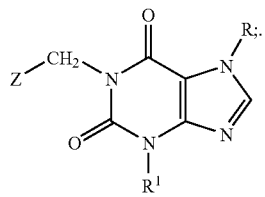

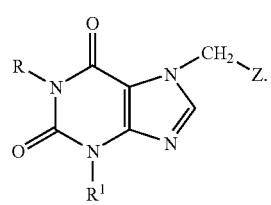

(H. J. Roth, Reaction of theophylline and theobromine with 1,2-epoxides, *Arch. Pharm.*, 1959, 292, pp. 234-238; *J. Med. Chem.*, 1985, 28, No. 5, p. 652).

In the interaction of IX and X with benzhydrylpiperazine and its derivatives, the compounds I and II on which a claim is made are derived, where X=OH and n=1 (Table 1).

The biological activity of the derivatives 1- and 7-[ω-(benzhydryl-4-piperazinyl-palkyl]-3-alkylxanthines (I and II).

The above and other features of the invention including various novel details of construction and combinations of parts, and other advantages, will now be more particularly described and pointed out in the claims. It will be understood that the particular method and device embodying the invention are shown by way of illustration and not as a limitation of the invention. The principles and features of this invention may be employed in various and numerous embodiments without departing from the scope of the invention.

DETAILED DESCRIPTION OF THE PREFERRED EMBODIMENTS

Study of the antihistaminic activity of the compounds on which a claim is made was done using known methodologies (*Rukovodstvo po eksperimental'nomu izucheniyu novykh farmakologicheskikh veshchestv [Manual on experimental study of new pharmacological substances]*, Moscow, 2005, p. 489) on isolated guinea pig ileum (suppression of the spasmogenic effect of histamine) and on anesthetized guinea pigs (antagonism in relation to the bronchoconstrictor effect of histamine). In tests on intact animals, substances were administered intravenously (5 minutes before the administration of histamine) and orally (2 hours before the beginning of the study).

In the evaluation of the duration of the antihistaminic effect, the compounds were administered orally 24-72 hours before the beginning of a study.

The most active compound, II-g (where R=H; R$^1$=CH$_3$; n=2; X=H; and Y=Y$^1$=H), was also studied in conscious guinea pigs using the model of itching induced by instillation of a histamine solution into the animal's eye (antihistamine effect), as well as in rats with the passive cutaneous anaphylaxis model (antiallergic effect). (*Rukovodstvo po eksperimental'nomu izucheniyu novykh farmakologicheskikh veshchestv* [Manual on experimental study of new pharmacological substances], Moscow, 2005, p. 511)

The compounds I and II on which a claim is made were studied in comparison with preparations that are similar in pharmacological effect and widely used in medical practice: cetirizine, loratadine, and azelastine (M. D. Mashkovsky, *Lekarstvennye sredstva [Drugs]*, Moscow, Novaya volna, 2005, 15$^{th}$ edition, pp. 285-297).

The compounds I and II on which a claim is made were studied in comparison with preparations that are similar in pharmacological effect and widely used in medical practice: cetirizine, loratadine, and azelastine (M. D. Mashkovsky, *Lekarstvennye sredstva [Drugs]*, Moscow, Novaya volna, 2005, 15$^{th}$ edition, pp. 285-297).

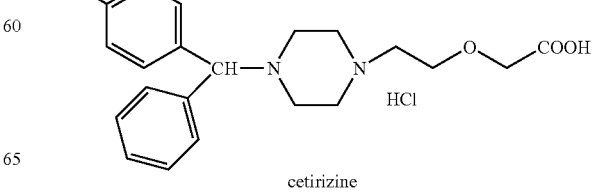

cetirizine

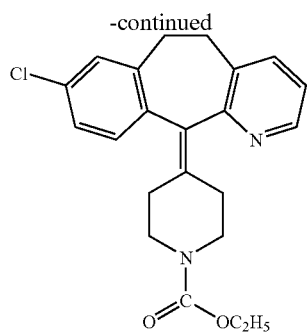

loratadine

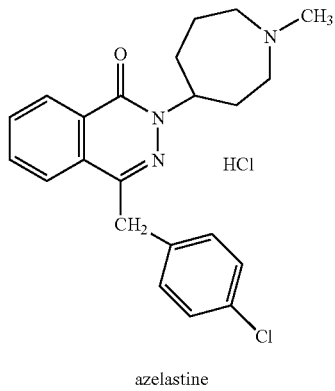

azelastine

Table 2 presents the results of the study of antihistaminic activity and toxicity of compounds I and II on which a claim is made.

As follows from the data presented, most of the compounds on which a claim is made are not inferior to cetirizine and loratadine in antihistaminic activity in both in vitro and in vivo conditions ($IC_{50}$ and $ED_{50}$, respectively), but are less active in comparison to azelastine. One exception is the II-g compound, which in isolated guinea pig ileum significantly surpasses cetirizine and loratadine with respect to activity, although it is somewhat inferior to azelastine. At the same time, in vivo conditions with intravenous administration, compound II-g is more active than all other preparations listed above; when administered orally (2 hours before beginning a test), compound II-g surpasses the potency of cetirizine and loratadine, and is similar to azelastine.

It must be emphasized that compound II-g, in regard to the duration of its antihistaminic activity, surpasses all agents to which it is compared, including azelastine. Thus, in the histamine bronchospasm model, compound II-g, cetirizine, loratadine, and azelastine provide effective blockade of $H_1$-histamine receptors after oral administration of a dose of 3 mg/kg, for 72, 48, 18 and 48 hours respectively. In the histamine-induced itch model, the protective effect of compound II-g at a dose of 3 mg/kg administered orally remains at a stable level for 2 days and decreases only after 72 hours, while the analogous effect of cetirizine and azelastine at the same dose already diminishes significantly after 48 hours and disappears altogether after 72 hours. In the passive cutaneous anaphylactic model, compound II-g and cetirizine at doses of 1 and 3 mg/kg, respectively, manifest a moderate and similar antiallergic effect.

A very important circumstance is the fact that compound II-g is less toxic than azelastine and cetirizine. Compound II-g is thermally stable, easily soluble in water, and, in contrast to loratadine, can be used for the manufacture both of solid drug forms and eye drops.

The results obtained make it possible to conclude that the series of derivatives of 1- and 7-[ω-(benzhydryl-4-piperazinyl-1)alkyl]-3-alkylxanthines (I and II), discovered and studied by us, and among which have been observed substances with high antihistaminic and antiallergic activity, opens up new prospects for treating allergic illnesses (Table 2).

A method is proposed to obtain xanthine derivatives, specifically 3-methyl-7-[4-(benzhydryl-4-piperazinyl-1)butyl] xanthine and its salts with organic and inorganic acids of general formula XI that have antihistaminic (antiallergic) activity.

The special-purpose compounds XI are synthesized from the 7-potassium salt of 3-methylxanthine (XII) by alkylation by 1,4-dibrombutane with subsequent interaction of the 7-(4-brombutyl)-3-methylxanthine (XIII) formed with 1-benzhydrylpiperazine (XIV) and neutralization of the derived base XI with organic or inorganic acid, in accordance with the diagram:

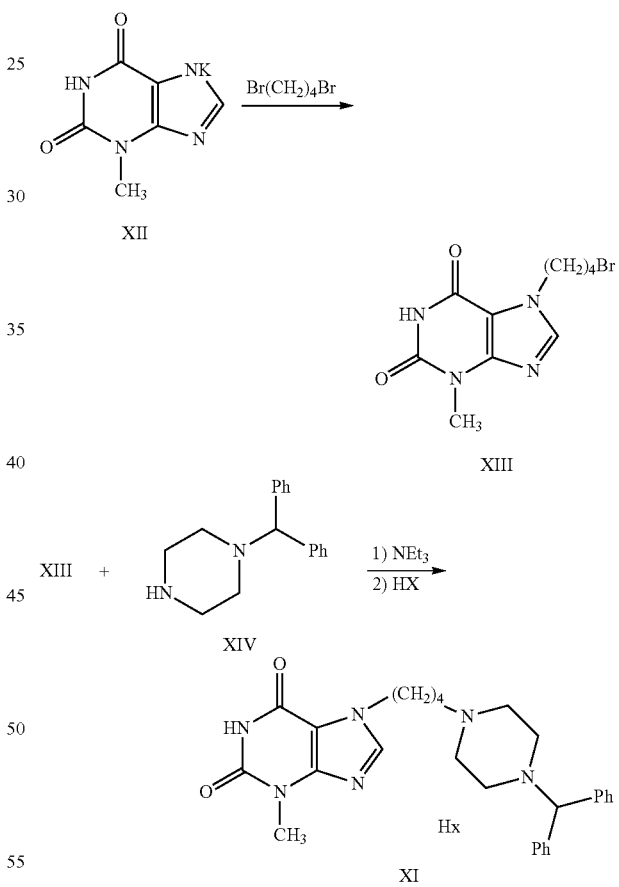

where the HX are organic or inorganic acids.

Considering that XIV and base XI can bind Hbr generated in the course of the reaction of XIII with XIV, initially attempts were undertaken to derive XI by heating XIII Significant progress in improving this reaction was achieved by interaction of XIII with XIV by heating with acetonitryl in the presence of triethylamine. In these conditions the process of deriving base XI ran smoothly and finished within 2-3 hours. The conversion of base XI to the corresponding salt was done by the usual methods used in preparative organic chemistry—by treating a solution or suspension of base XI with a solution of organic or inorganic acid.

Regardless of the fact that all derived salts (XI) were of equal value with respect to the pharmacological (antihistaminic) activity, XI in the form of a salt with succinic acid (succinate) turned out to be the most convenient for practical use and have good pharmacotherapeutic properties (absence of hygroscopicity, good thermal stability, solubility in water, and required pH of the aqueous solution).

Speaking of the usefulness of the compounds being claimed and, in particular, 7-/4-(4-benzhydrylpiperazinyl-1) butyl/-3-methylxanthine succinate (XI, HX—succinic acid), it must be emphasized that this compound in its pharmacotherapeutic properties (activity and duration of $H_t$-histamine receptor blockade, low toxicity, solubility in water) surpasses current antihistamine (antiallergic) preparations: cetirizine, loratadine, and azelastine.

EXAMPLE 1

Derivation of 1-(4-brombutyl)-3-methyl-7-benzylxanthine (VI-j, R=$CH_2$Ph; $R^1$=$CH_3$, n=4).

To 60 mL of absolute $CH_3OH$, containing 2.79 g (0.0517 mole) of sodium methylate, are added 10.0 g (0.039 mole) of 3-methyl-7-benzylxanthine (III, where R=$CH_2$Ph, $R^1$=$CH_3$).

The suspension is boiled 30 minutes while stirring and the reaction mass is stripped to dryness; at the end of the process, methanol residues are eliminated by evaporation of toluol and 10.86 g of the 1-sodium salt of 3-methyl-7-benzylxanthine are obtained.

To a solution of 42.3 g (24.4 mL; 0.196 mole) of 1,4-dibrombutane in 100 mL of dimethylformamide (DMFA) are added 10.86 g (0.039 mole) of the 1-sodium salt of 3-methyl-7-benzylxanthine and boiled)(~150° while stirring for 3.5 hours. The mass is stripped off in vacuum; water and benzene are added to the residue and stirred, the benzene layer is removed, and the remainder is washed with water, dried over sodium sulfate and filtered through a layer of aluminum oxide. The filtrate is stripped to a volume of ~30 mL and an equal quantity of hexane is added. The precipitate is filtered out and dried. This yields 12.16 g (79.6%) of 1-(4-brombutyl)-3-methyl-7-benzylxanthine, melting point 90-92° (from methanol), $M^+$ 391.

EXAMPLE 2

Derivation of 3-methyl-7-(4-brombutyl)xanthine (VII-j, R=H, $R^1$=$CH_3$, n=4).

To a solution of 42.3 g (0.196 mole; 23.4 mL) of 1,4-dibrombutane in 100 mL of acetonitrile are added 10.0 g (0.049 mole) of the 7-potassium salt of 3-methylxanthine. The suspension is boiled while stirring 28 hours and then cooled, and the precipitate is filtered out, washed to a neutral reaction with water and then methanol, and then dried. This yields 9.0 g (61%) of technical 3-methyl-7-(4-brombutyl) xanthine (VII, R=H, $R^1$=$CH_3$, n=4), after two-fold purification of the technical specimen by crystallization from the mixture of benzene and methanol, and then of dimethylsulfoxide, with melting point 218-220°, $M^+$ 301.

Other VI and VII [compounds] are synthesized analogously (see Table 3).

EXAMPLE 3

Derivation of 1-(2,3-epoxypropyl)-3,7-dimethylxanthine (IX, where

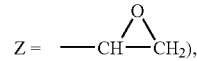

and R=$R^1$=$CH_3$). A suspension of 3 g (0.148 mole) of the sodium salt of 3,7-dimethylxanthine (III, 1-Na salt; R=$R^1$=$CH_3$) and 20 mL of epichlorhydrin is heated while stirring at 65-70° for 20 hours. After cooling, the precipitate is filtered out and washed with methylene chloride. The derived solution of IX in methylene chloride is stripped and the grease-like residue is kneaded in absolute ether, yielding 2.7 (77%) of 1-(2,3-epoxypropyl)-3,7-dimethylxanthine, melting point 115-119°, $M^+$ 236 (J-C. Pascal et al, *J. Med. Chem.,* 1985, No. 28, No. 5, pp. 647-652, melting point 116-117°).

In a similar manner, from the Na salt of 3-methyl-7-benzylxanthine (III, 1-Na salt, R=$CH_2$Ph; $R^1$=$CH_3$) is synthesized 1-(2,3-epoxypropyl)-3-methyl-7-benzylxanthine (IX, where

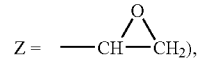

R=$CH_2$Ph; $R^1$=$CH_3$), yield 80%, melting point 90-95°, $M^+$ 312.

EXAMPLE 4

Derivation of -7-(4-brombutyl)-3-methylxanthine (XIII).

To a solution of 42.2 g (0.196 mole; 23.4 mL) of 1,4-dibrombutane in 100 mL of acetonitrile are added 10 g (0.049 mole) of 7-potassium salt of 3-methylxanthine (M. V. Rubtsov and A. G. Baychikov. *Sinteticheskiye khimiko-farmatsevticheskiye preparaty* [Synthetic chemical and pharmaceutical preparations]. Meditsina, Moscow, 1971, p. 288). The suspension is boiled while stirring for 28 hours and cooled to room temperature, and the precipitate is filtered out, washed to a neutral reaction with water and then with methanol, and dried. This yields 9.0 g (61%) of technical 7-(4-brombutyl)-3-methylxanthine; after crystallization from the mixture of benzene-methanol, and then dimethylsulfoxide. Melting point 218-220 C; $M^+$ 301.

EXAMPLE 5

Derivation of 7-/4-(4-benzhydrylpiperazinyl-1)butyl/-3-methylxanthine.

A suspension of 50 g of 92% XIII, 43.7 g of 97% XIV, and 23.4 mL of triethylamine in 750 mL of acetonitrile is boiled while stirring 3 hours. The reaction mass is cooled to room temperature and filtered, and the precipitate is carefully washed in water, acetonitrile, and isopropanol, and dried, yielding 65.9 g of the base 7-/4-(4-benzhydrylpiperazinyl-1) butyl/-3-methylxanthine, melting point 193-194 C (from methanol).

Computed, %: C, 68.62; H, 6.83; N, 17.78.
$C_{27}H_{32}N_6O_2$
Found, %: C, 68.41; H, 6.93; N, 17.78.
NMR [nuclear magnetic resonance] spectrum ($CDCl_3$, δ, ppm): 1.46 (m[multiplet], 2H, γ-$CH_2$); 1.87 (M, 2H, β-$CH_2$;

2.35 (t[triplet], 2H, δ-CH$_2$); 4.23 (t, 2H, α-CH$_2$); 2.15-2.60 (ws [widened singlet], 8H-protons of the piperazine cycle); 3.51 (s, 3H, NCH$_3$); 4.17 (C, 1H, CH); 7.10-7.42/m, 10H, 2 (C$_6$H$_5$)/; 7.53 (s, 1H, C$_8$H); 9.00 (ws, 1H, NH).

Mass spectrum (EI [electron impact], 70 eV), m/z: 472/M/$^+$

Dihydrochloride, melting point 220-222 C (from 90% ethanol); pH of aqueous solution 2.45.

Computed, %: C, 59.45; H, 6.28; N, 15.40

C$_{27}$H$_{34}$N$_6$O$_2$Cl$_2$

Found, %: C, 58.84; H, 6.60; N, 15.28; H$_2$O 2.30

Succinate, melting point 187-189 C (from 95% ethanol); pH of aqueous solution 4.85.

Computed, %: C, 63.04; H, 6.48; N, 14.23.

C$_{31}$H$_{38}$N$_6$O$_6$

Found, %: C, 62.88; H, 6.74; N, 14.17

UV spectrum. (95% ethanol): $_{max}$ 273 nm, $_{min}$ 245 nm

Oxalate, melting point 128-130 C (from acetone); pH of aqueous solution 3.44

Computed, %: C, 61.91; H, 6.09; N, 14.94

C$_{29}$H$_{34}$N$_6$O$_6$

Found, %: C, 61.45; H, 6.83; N, 14.94.

EXAMPLE 6

Derivation of 1-[4-(benzhydryl-4-piperazinyl-1)butyl]-3-methylxanthine dihydrochloride (I, where R=H, R$^1$=CH$_3$, X=H, n=2, Y=Y$^1$=H) from 7-benzyl-1-(4-brombutyl)-3-methylxanthine (VI, where R=benzyl, R$^1$=Me).

Derivation of 1-[4-(benzhydryl-4-piperazinyl-1)butyl]-3-methylxanthine dihydrochloride (I, where R=H, R$^1$=CH$_3$, X=H, n=2, Y=Y$^1$=H) from 7-benzyl-1-(4-brombutyl)-3-methylxanthine (VI, where R=benzyl, R$^1$=Me).

A solution of 2.1 g (0.005 mole) of 95% 7-benzyl-1-(4-brombutyl)-3-methylxanthine in 50 mL methanol and 0.21 g of 20% palladium hydroxide on carbon is hydrated at 40° until cessation of hydrogen absorption (~1.5 hours). The catalyst is filtered out and washed with hot methanol, then the filtrate is evaporated, yielding 1.35 g of 1-(4-brombutyl)-3-methylxanthine (VI, where R=H, R$^1$=Me, n=4).

A mixture of 1.35 g of the latter, 1.13 g (0.045 mole) of benzhydrylpiperazine (VIII, where Y=Y$^1$=H), 0.036 (0.00022 mole) of potassium iodide and 30 mL of acetonitrile are boiled while stirring 15 hours. The reaction mass is evaporated and the precipitate is dissolved in 25 mL of 5% hydrochloric acid, then the solution is washed with chloroform and the hydrochloric acid solution is alkalized with solid sodium bicarbonate to a pH of ~8. The mass obtained is extracted with chloroform, the extract is washed with saturated aqueous solution of sodium chloride and dried with magnesium sulfate.

The chloroform solution is evaporated and the precipitate is dissolved in 5 mL of isopropanol, then saturated hydrochloric acid solution is added in the isopropanol, to a pH of 2. After cooling (5-7°, 16 hours), the precipitate is filtered and crystallized from the methanol-isopropanol mixture, yielding 1.38 g (50.7%) of 1-[4-(benzhydryl-4-piperazinyl-1)butyl]-3-methylxanthine dihydrochloride, melting point 198-198°.

Found %: C, 59.41; H, 6.54; N, 15.06.

C$_{27}$H$_{32}$N$_6$O$_2$.2 HCl

Computed %: C, 59.45; H, 6.28; N, 15.40.

In a similar manner, 1-[4-(benzhydryl-4-piperazinyl-1)butyl]-3-butylxanthine dihydrochloride (I, where R=H, R=N-Bu, X=H, n=2, Y=Y$^1$=H) is obtained from 1-(4-brombutyl)-3-butyl-7-benzylxanthine (VI, where R=CH$_2$Ph; R$^1$=n-Bu; n=4) and benzhydrylpiperazine (VIII, where Y=Y$^1$=H), yield 42.2%, melting point 215-217°; M$^+$ 514.

Found %: C, 60.29; H, 7.44; N, 13.93; H$_2$O 2.55.

C$_{30}$H$_{38}$N$_6$O$_2$.2 HCl.0.75H$_2$O

Computed %: C, 59.94; H, 7.04; N, 13.98; H$_2$O 2.25.

EXAMPLE 7

Derivation of 1,3-dimethyl-7-[2-oxy-3-(benzhydryl-4-piperazinyl-1)propyl]xanthine dihydrochloride (II, where R=CH$_3$, n=1, X=OH, Y=Y$^1$=H)

A mixture of 2.45 g (0.009 mole) of 1,3-dimethyl-7-(2-oxy-3-chlorpropyl)xanthine (X, where Z=—CH(OH)—CH$_2$Cl) (see H. J. Roth, Arch. Pharm., 1959, 292, pp. 234-238), 2.27 g (0.009 mole) of benzhydrylpiperazine (VIII, where Y=Y$^1$=H), 1.38 g of potash, 0.08 g (0.00005 mole) of potassium iodide, and 50 mL of acetonitrile is boiled while stirring 20 hours. The mass is evaporated, the precipitate is dissolved in chloroform, the solution is washed with water, and dried with magnesium sulfate. After distilling off of the chloroform, the precipitate is crystallized from ethyl acetate, yielding 2.61 g of base II (where R=R$^1$=CH$_3$; n=1, X=OH, Y=Y$^1$=H), which is dissolved in 70 mL of isopropanol. A solution of hydrochloric acid in isopropanol is added to the solution obtained to a pH of ~2, and the precipitate is filtered out and dried. This yields 3.34 (66%) of 1,3-dimethyl-7-[2-oxy-3-(benzhydryl-4-piperazinyl-1)propyl]xanthine dihydrochloride, melting point 224-226°.

Found %: C, 57.32; H, 6.10; N, 14.86.

C$_{27}$H$_{32}$N$_6$O$_3$.2HCl

Computed %: C, 57.75; H, 6.10; N, 14.97.

EXAMPLE 8

Derivation of 1,3-dimethyl-7-[2-carboxyethylcarbonyloxy-3-(benzhydryl-4-piperazinyl-1)propyl]xanthine (II, where R=R$^1$=CH$_3$; n=1; X=OCOCH$_2$CH$_2$COOH; Y=Y$^1$=H).

A mixture of 2.0 g (0.004 mole) of 1,3-dimethyl-7-[2-oxy-3(benzhydryl-4-piperazinyl-1)propyl]xanthine (II, where R=R$^1$=CH$_3$; n=1; X=OH; Y=Y$^1$=H), 0.5 g (0.005 mole) of anhydride of succinic acid, and 20 mL of dichlorethane is boiled for 4 hours and stripped until dry. The residue is crystallized from absolute ethanol, yielding 2.04 g (86.7%) of 1,3-dimethyl-7-[2-carboxyethylcarbonyloxy)-3-(benzhydryl-4-piperazinyl-1)propyl]xanthine, melting point 183-185°.

Found %: C, 63.28; H, 6.53; N, 14.32.

C$_{31}$H$_{36}$N$_6$O$_2$.

Computed %: C, 63.25; H, 6.16; N, 14.28.

EXAMPLE 9

Derivation of 1-[2-oxy-3-(benzhydryl-4-piperazinyl-1)propyl]-3,7-dimethylxanthine dihydrochloride I (R=R$^1$=CH$_3$; n=1; X=OH; Y=Y$^1$=H).

A mixture of 1 g (0.004 mole) of 1-(2,3-epoxypropyl)-3,7-dimethylxanthine, 1.26 g (0.0044 mole) of benzhydrylpiperazine, and 30 mL isopropanol is boiled while stirring 30 hours. After cooling, the precipitate is filtered, washed with ether, and dried. This yields 1.96 g (95%) of 1-[2-oxy-3-(benzhydryl-4-piperazinyl-1)propyl]-3,7-dimethylxanthine:

base, melting point 120-122°, M$^+$ 488;

dihydrochloride, melting point 196-198°; M$^+$ 488.

In a similar manner the following are synthesized:

1-[2-oxy-3-(4$^1$-chlorbenzhydryl-4-piperazinyl-1)propyl]-3,7-dimethylxanthine (I, where R=R$^1$=CH$_3$; n=1; X=OH; Y=Cl; Y$^1$=H):

base, yield 67%, melting point 152-155°;

dihydrochloride, melting point 192-194°.

1-[2-oxy-3-(benzhydryl-4-piperazinyl-1)-propyl]-3-methyl-7-benzylxanthine (I, where R=CH$_2$Ph, R$^1$=Me; n=1; X=OH; Y=Y$^1$=H), yield 50%, melting point 98-100°.

1-[2-oxy-3-(4$^1$-chlorbenzhydryl-4-piperazinyl-1)propyl]-3-methyl-7-benzylxanthine (I, where R=CH$_2$Ph, R$^1$=Me; n=1; X=OH; Y=Cl; Y$^1$=H), yield 50%, melting point 170-172°.

These substances expand the formulary of long-acting antihistaminic (antiallergic) medications, and the method proposed makes it possible to shorten the time to carry out the complete process cycle in comparison with known methods.

TABLE 1

Derivatives of 1- and 7-[ω-(benzhydryl-4-piperazinyl-1)alkyl]-3-methylxanthine (I and II, where $R^1 = CH_3$)

| Compound | n | X | Y | $Y^1$ | R | Molecular formula | Melting point, °C. | Mass spectrum EI m/z; $M^{+o}$ |
|---|---|---|---|---|---|---|---|---|
| 1 | 2 | 3 | 4 | 5 | 6 | 7 | 8 | 9 |
| I-a | 0 | H | H | H | $CH_2Ph$ | $C_{32}H_{34}N_6O_2 \cdot 2HCl \cdot H_2O$ | 200-210 | 534 |
| I-b | 1 | H | H | H | $CH_2Ph$ | $C_{33}H_{36}N_6O_2 \cdot 2HCl$ | 187-189 | 548 |
| I-c | 1 | H | H | Cl | $CH_2Ph$ | $C_{33}H_{35}ClN_6O_2 \cdot 2HCl \cdot 0.5H_2O$ | 189-192 | 582 |
| I-d | 1 | H | F | F | $CH_2Ph$ | $C_{33}H_{34}F_2N_6O_2 \cdot 2HCl$ | 176-178 | 584 |
| I-e | 1 | H | H | H | $4-FC_6H_4CH_2$ | $C_{33}H_{35}FN_6O_2 \cdot 2HCl$ | 224-226 | 566 |
| I-f | 1 | H | F | F | $4-FC_6H_4CH_2$ | $C_{33}H_{33}F_3N_6O_2 \cdot 2HCl$ | 178-180 | 602 |
| I-g | 1 | H | H | H | $CH_2CO_2H$ | $C_{28}H_{32}N_6O_4 \cdot H_2O$ | 153-155 | 516 |
| I-h | 1 | H | H | H | $CH_2CO_2K$ | $C_{28}H_{31}KN_6O_4 \cdot 1.5H_2O$ | 146-148 | — |
| I-i | 2 | H | H | H | $CH_2Ph$ | $C_{34}H_{38}N_6O_2 \cdot 2HCl$ | 145-146 | 562 |
| I-j | 2 | H | H | H | $4-FC_6H_4CH_2$ | $C_{34}H_{37}FN_6O_2 \cdot 2HCl$ | 154-157 | 580 |
| I-k | 2 | H | F | F | $4-FC_6H_4CH_2$ | $C_{34}H_{35}F_3N_6O_2 \cdot 2HCl$ | 134-136 | 616 |
| I-l | 2 | H | F | F | $CH_2Ph$ | $C_{34}H_{36}F_2N_6O_2 \cdot 2HCl \cdot 1.5H_2O$ | 171-173 | 598 |
| I-m | 3 | H | H | H | $CH_2Ph$ | $C_{35}H_{40}N_6O_2 \cdot 2HCl$ | 207-208 | 576 |
| I-n | 3 | H | F | F | $CH_2Ph$ | $C_{35}H_{38}F_2N_6O_2 \cdot 2HCl$ | 189-192 | 612 |
| I-o | 3 | H | H | H | H | $C_{25}H_{28}N_6O_2 \cdot 2HCl \cdot 0.5H_2O$ | 210-212 | 444 |
| I-p | 0 | H | F | F | H | $C_{25}H_{26}F_2N_6O_2 \cdot 2HCl$ | 202-205 | 480 |
| I-q | 1 | H | H | H | H | $C_{26}H_{30}N_6O_2 \cdot 2HCl \cdot H_2O$ | 205-207 | 458 |
| I-r | 1 | H | F | F | H | $C_{26}H_{28}F_2N_6O_2 \cdot 2HCl$ | 215-220 | 494 |
| I-s | 2 | H | H | H | H | $C_{27}H_{32}N_6O_2 \cdot 2HCl$ | 196-198 | 472 |
| I-t | 2 | H | H | Cl | H | $C_{27}H_{31}ClN_6O_2 \cdot 2HCl \cdot H_2O$ | 192-194 | 506 |
| I-u | 2 | H | F | F | H | $C_{27}H_{30}F_2N_6O_2 \cdot 2HCl \cdot 0.5H_2O$ | 202-206 | 508 |
| I-v | 2 | H | H | H | $CH_3$ | $C_{28}H_{34}N_6O_2 \cdot 2HCl$ | 171-174 | 486 |
| I-w | 3 | H | H | H | $CH_3$ | $C_{28}H_{34}N_6O_2 \cdot 2HCl$ | 241-242 | 486 |
| I-x | 1 | OH | H | H | $CH_3$ | $C_{27}H_{32}N_6O_3 \cdot 2HCl \cdot 2H_2O$ | 196-198 | 488 |
| I-y | 1 | OH | H | Cl | $CH_3$ | $C_{27}H_{31}ClN_6O_3 \cdot 2HCl \cdot 1.5H_2O$ | 192-194 | 522 |
| I-z | 1 | OH | H | H | $CH_2Ph$ | $C_{33}H_{36}N_6O_3$ | 98-100 | 564 |
| I-aa | 1 | OH | H | Cl | $CH_2Ph$ | $C_{33}H_{35}ClN_6O_3$ | 170-172 | 598 |
| II-a | 0 | H | H | H | $CH_3$ | $C_{26}H_{30}N_6O_2 \cdot 2HCl$ | 240-242 | 458 |
| II-b | 0 | H | H | Cl | $CH_3$ | $C_{26}H_{29}ClN_6O_2 \cdot 2HCl$ | 241-243 | 492 |
| II-c | 0 | H | F | F | $CH_3$ | $C_{26}H_{28}F_2N_6O_2 \cdot 2HCl$ | 237-238 | 494 |
| II-d | 1 | H | H | H | $CH_3$ | $C_{27}H_{32}N_6O_2 \cdot 2HCl$ | 238-240 | 472 |
| II-e | 1 | H | H | H | H | $C_{26}H_{30}N_6O_2 \cdot 2HCl$ | 258-260 | 458 |
| II-f | 2 | H | H | H | $CH_3$ | $C_{28}H_{34}N_6O_2 \cdot 2HCl$ | 224-226 | 486 |
| II-g | 2 | H | H | H | H | $C_{27}H_{32}N_6O_2 \cdot 2HCl \cdot 1.5H_2O$ | 216-217 | 472 |
| II-h | 1 | OH | H | H | $CH_3$ | $C_{27}H_{32}N_6O_3 \cdot 2HCl$ | 244-246 | 488 |
| II-i | 1 | OH | H | Cl | $CH_3$ | $C_{27}H_{31}ClN_6O_3 \cdot 2HCl \cdot H_2O$ | 232-234 | 522 |
| II-j | 1 | OH | F | F | $CH_3$ | $C_{27}H_{30}F_2N_6O_2 \cdot 2HCl$ | 225-227 | 524 |

TABLE 2

Antihistaminic activity and acute toxicity of 1- and 7-[ω-(benzhydryl-4-piperazinyl-1)alkyl]-3-methylxanthines (I and II, where $R^1 = CH_3$)

| Compound | Isolated ileum of guinea pig, $IC_{50}$ (M) | Guinea pigs, in vivo Intravenous administration, $ED_{50}$ mg/kg | Guinea pigs, in vivo Peroral administration, $ED_{50}$ mg/kg | Acute toxicity, $LD_{50}$, mg/kg mice perorally |
|---|---|---|---|---|
| 1 | 2 | 3 | 4 | 5 |
| I-a | $7.92 \pm 2.6 \cdot 10^{-7}$ | | | >1000.0 |
| I-b | $1.26 \pm 0.33 \cdot 10^{-7}$ | 0.3 | | >800.0 |
| I-c | $1.33 \pm 0.13 \cdot 10^{-7}$ | | | 400.0 |
| I-d | $1.14 \pm 0.25 \cdot 10^{-7}$ | 0.6 | 3.0 | >250.0 |
| I-e | $4.3 \pm 0.71 \cdot 10^{-7}$ | | | |
| I-f | $5.14 \pm 0.72 \cdot 10^{-7}$ | | | |
| I-g | $2.44 \pm 0.73 \cdot 10^{-7}$ | | | |
| I-h | $2.22 \pm 0.51 \cdot 10^{-7}$ | | | >1000.0 |
| I-i | $1.11 \pm 0.12 \cdot 10^{-7}$ | 0.2 | 0.3 | 400.0 |
| I-j | $2.27 \pm 0.37 \cdot 10^{-7}$ | | | 400.0 |
| I-k | $2.67 \pm 0.18 \cdot 10^{-7}$ | | | 400.0 |
| I-l | $1.85 \pm 0.56 \cdot 10^{-7}$ | 0.5 | 0.5 | >1000.0 |
| I-m | $0.92 \pm 0.17 \cdot 10^{-7}$ | | | >200.0 |
| I-n | $2.53 \pm 0.34 \cdot 10^{-7}$ | 1.2 | 3.0 | 250 |
| I-o | $1.62 \pm 0.16 \cdot 10^{-7}$ | | | >1000.0 |
| I-p | $1.92 \pm 0.14 \cdot 10^{-7}$ | 1.5 | | |
| I-q | $0.42 \pm 0.08 \cdot 10^{-7}$ | 0.4 | | >1000.0 |
| I-r | $0.76 \pm 0.15 \cdot 10^{-7}$ | | >3.0 | >1000.0 |
| I-s | $0.26 \pm 0.02 \cdot 10^{-7}$ | 0.2 | 0.3 | >750.0 |
| I-t | $1.04 \pm 0.29 \cdot 10^{-7}$ | 0.3 | | >1000.0 |
| I-u | $0.51 \pm 0.11 \cdot 10^{-7}$ | 0.7 | >3.0 | >1000.0 |
| I-v | $0.32 \pm 0.03 \cdot 10^{-7}$ | 0.2 | >1.5 | >1000.0 |
| I-w | $0.74 \pm 0.11 \cdot 10^{-7}$ | 0.1 | | |
| I-x | $12.7 \pm 3.7 \cdot 10^{-7}$ | | | |
| I-y | $1.23 \pm 0.07 \cdot 10^{-7}$ | | | |
| I-z | $5.24 \pm 0.06 \cdot 10^{-7}$ | | | |
| I-aa | $5.36 \pm 1.62 \cdot 10^{-7}$ | | | |
| II-a | $0.14 \pm 0.02 \cdot 10^{-7}$ | 0.1 | | |
| II-b | $0.32 \pm 0.11 \cdot 10^{-7}$ | | | >125.0 |
| II-c | $0.17 \pm 0.04 \cdot 10^{-7}$ | 0.2 | 8.0 | >1000.0 |
| II-d | $0.12 \pm 0.02 \cdot 10^{-7}$ | 0.05 | | >1000.0 |
| II-e | $0.19 \pm 0.02 \cdot 10^{-7}$ | 0.1 | | 900.0 |
| II-f | $0.17 \pm 0.04 \cdot 10^{-7}$ | 0.1 | <1.5 | 750.0 |
| II-g | $0.18 \pm 0.04 \cdot 10^{-7}$ | 0.02 | 0.02 | 1300.0 |

TABLE 2-continued

Antihistaminic activity and acute toxicity of
1- and 7-[ω-(benzhydryl-4-piperazinyl-1)alkyl]-3-methylxanthines
(I and II, where $R^1 = CH_3$)

| Compound 1 | Isolated ileum of guinea pig, $IC_{50}$ (M) 2 | Antihistaminic activity Guinea pigs, in vivo | | Acute toxicity, $LD_{50}$, mg/kg mice perorally 5 |
|---|---|---|---|---|
| | | Intravenous administration, $ED_{50}$ mg/kg 3 | Peroral administration, $ED_{50}$ mg/kg 4 | |
| II-h | 1.59 ± 0.22 · 10 − 7 | 0.1 | 2.0 | >1000.0 |
| II-i | 2.94 ± 0.73 · 10 − 7 | | | >1000.0 |
| II-j | 1.47 ± 0.51 · 10 − 7 | | | >1000.0 |
| Cetirizine | 1.27 ± 0.55 · 10 − 7 | 0.07 | 0.2 | 404.5 |
| Loratadine | 4.72 ± 1.35 · 10 − 7 | 0.3 | 0.9 | 4000.0* |
| Azelastine | 0.07 ± 0.004 · 10 − 7 | 0.05 | 0.015 | 124-139** $\begin{pmatrix} O\!-\!O \end{pmatrix}$ |

*Dridi D. et al, Circadian time-dependent differences in murine tolerance to the antihistaminic agent loratidine, Chronobiol Int., 2005, 22 (3), 499-514.
**Zechel H. J. et al, Pharmacological and toxicological properties of azelastine, a novel antiallergic agent, Arzneimittelforschung, 1981, 31 (8), 1184-1193.

TABLE 3

| Compound 1 | n 2 | R 3 | $R^1$ 4 | Yield, % 5 | Melting point, ° C. 6 | Mass spectrum, EI, m/z; $M^+$ 7 |
|---|---|---|---|---|---|---|
| VI-a | 2 | $CH_2Ph$ | $CH_3$ | 65 | 77-79 | 363 |
| VI-b | 3 | $CH_2Ph$ | $CH_3$ | 70 | 81-83 | 377 |
| VI-e | 3 | $4\text{-}FC_6H_4CH_2$ | $CH_3$ | 66 | 123-125 | 395 |
| VI-m | 4 | $4\text{-}FC_6H_4CH_2$ | $CH_3$ | 67 | 92-94 | 409 |
| VI-n | 5 | $CH_2Ph$ | $CH_3$ | 59 | 96-98 | 405 |
| VI-w | 4 | $CH_3$ | $CH_3$ | 60 | 120-122 | 315 |
| VI | 4 | $CH_2Ph$ | $H\!-\!C_4H_9$ | 75 | 88-90 | 433 |
| VII-a | 2 | $CH_3$ | $CH_3$ | 70 | 143-145 | 287 |
| VII-d | 3 | $CH_3$ | $CH_3$ | 60 | 131-133 | 301 |
| VII-e | 3 | H | $CH_3$ | 60 | 126-128 | 287 |
| VII-i | 4 | $CH_3$ | $CH_3$ | 65 | 123-125 | 315 |
| VII | 4 | H | $H\!-\!C_4H_9$ | 59 | 86-88 | 343 |

While this invention has been particularly shown and described with references to preferred embodiments thereof, it will be understood by those skilled in the art that various changes in form and details may be made therein without departing from the scope of the invention encompassed by the appended claims.

What is claimed is:

1. 7-[4-(benzhydrylpiperazinyl-1)butyl]-3-methylxanthine dihydrochloride capable of producing an antihistaminic and antiallergenic effect:

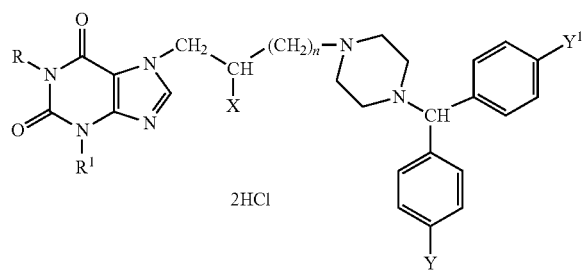

2HCl wherein R is H; wherein $R^1$ is Me; wherein n =2; wherein X is H; and wherein Y is H and $Y^1$ is H.

2. 7-[4-(benzhydrylpiperazinyl-1)butyl]-3-methylxanthine or a pharmaceutically acceptable salt or hydrate thereof, capable of producing an antihistaminic and antiallergenic effect, of formula II:

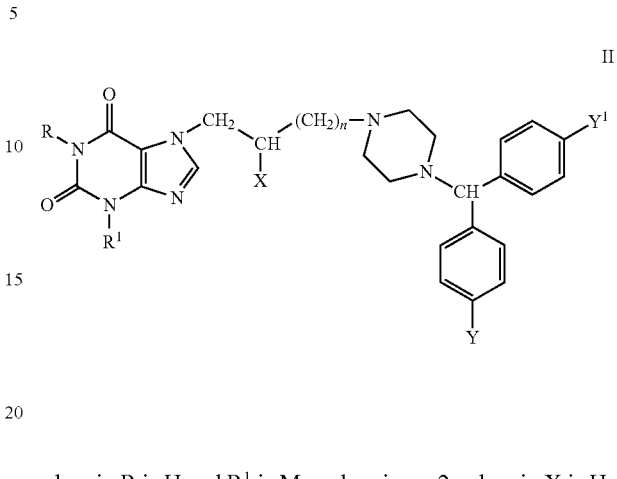

wherein R is H and $R^1$ is Me; wherein n =2; wherein X is H; and wherein Y is H and $Y^1$ is H.

3. 7-[4-(benzhydrylpiperazinyl-1)butyl]-3-methylxanthine oxalate, capable of producing an antihistaminic and antiallergenic effect, of formula II:

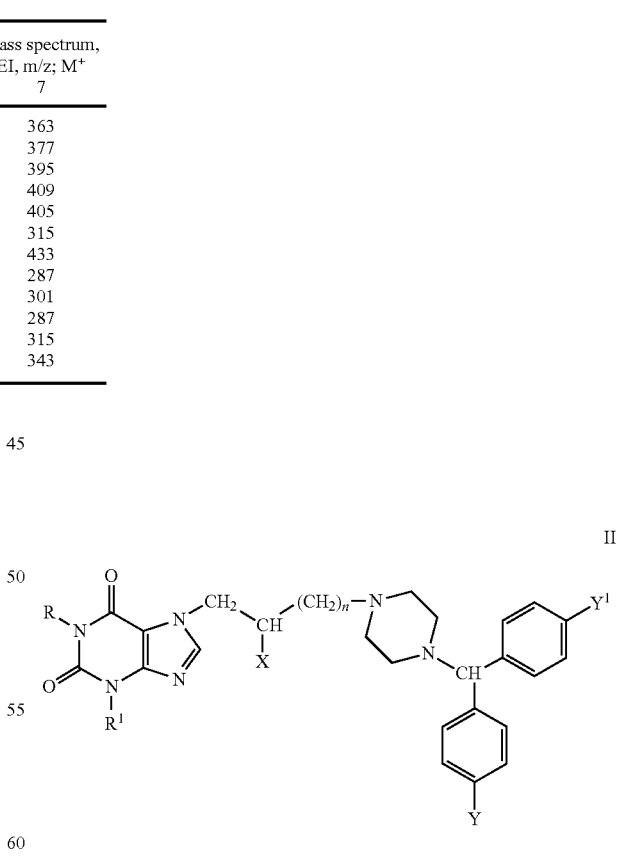

wherein R is H and $R^1$ is Me; wherein n =2; wherein X is H; wherein Y is H and $Y^1$ is H; and the compound as an oxalate salt.

4. 7-[4-(benzhydrylpiperazinyl-1)butyl]-3-methylxanthine succinate, capable of producing an antihistaminic and antiallergenic effect, of formula II:

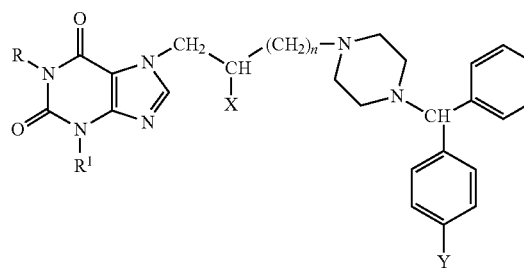

wherein R is H and R¹ is Me; wherein n =2; wherein X is H; wherein Y is H and Y¹ is H; and the compound as a succinate salt.

5. A compound 7-[4-(benzhydrylpiperazinyl-1)butyl]-3-methylxanthine of formula:

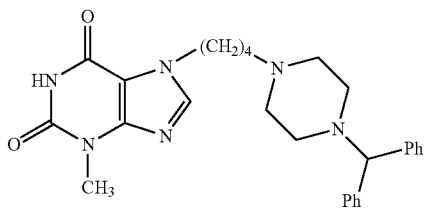

made by a process comprising:
alkylating the 7-potassium salt of 3-methylxanthine with 1,4-dibromobutane to produce 7-(4-bromobutyl)-3-methylxanthine, and reacting the 7-(4-bromobutyl)-3-methylxanthine with 1-benzhydrylpiperazine to produce 7-[4-(4-benzhydryl-piperazinyl-1)butyl]-3-methylxanthine.

6. The compound according to claim 5, wherein alkylating the 7-potassium salt of 3-methylxanthine with the 1,4-dibromobutane, as well as reacting the 7-(4-bromobutyl)-3-methylxanthine with the 1-benzhydrylxanthine takes place in an organic solvent.

7. The compound according to claim 5, wherein reacting the 7-(4-bromobutyl)-3-methylxanthine with the 1-benzhydrylpiperazine takes place in the presence of an organic base.

8. The compound according to claim 6, wherein the organic solvent is acetonitrile.

9. The compound according to claim 6, wherein reacting the 7-(4-bromobutyl)-3-methylxanthine with the 1-benzhydrylpiperazine takes place in the presence of an organic base.

10. The compound according to claim 9, wherein the organic base is triethylamine.

11. A method of producing 7-[4-(benzhydryl-4-piperazinyl-1)butyl]-3-methylxanthine of formula:

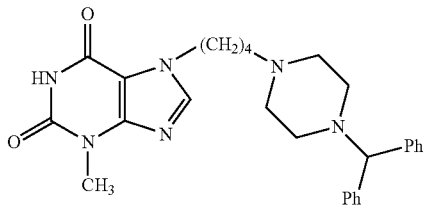

comprising:
alkylating the 7-potassium salt of 3-methylxanthine with 1,4-dibromobutane to produce 7-(4-bromobutyl)-3-methylxanthine, wherein alkylating the 7-potassium salt of 3-methylxanthine takes place with a four-fold molar excess of 1,4-dibromobutane; and reacting the 7-(4-bromobutyl)- 3-methylxanthine with 1-benzhydrylpiperazine to produce 7-[4-(4-benzhydryl-piperazinyl-1)butyl]-3-methylxanthine.

12. The method according to claim 11, wherein alkylating the 7-potassium salt of 3-methylxanthine takes place with the four-fold molar excess of the 1,4-dibromobutane takes place in an organic solvent; and reacting the 7-(4-bromobutyl)-3-methylxanthine with the 1-benzhydrylxanthine takes place in the organic solvent.

13. The method according to claim 11, wherein reacting the 7-(4-bromobutyl) -3-methylxanthine with the 1-benzhydrylpiperazine takes place in the presence of an organic base.

14. The method according to claim 12, wherein the organic solvent is acetonitrile.

15. The method according to claim 12, wherein reacting the 7-(4-bromobutyl) -3-methylxanthine with the 1-benzhydrylpiperazine takes place in the presence of an organic base.

16. The method according to claim 15, wherein the organic base is triethylamine.

17. A method of producing a salt of 7-[4-(benzhydryl-piperazinyl-1)butyl]-3-methylxanthine of formula XI:

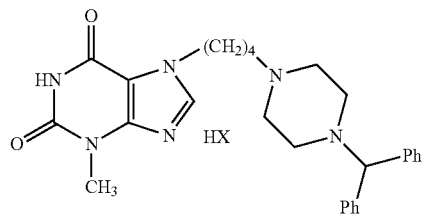

where HX is an organic acid or inorganic acid, comprising:
alkylating the 7-potassium salt of 3-methylxanthine with a four-fold molar excess of 1,4-dibromobutane to produce 7-(4-bromobutyl)-3-methylxanthine; reacting the 7-(4-bromobutyl)- 3-methylxanthine with 1-benzhydrylpiperazine to produce 7-[4-(4-benzhydryl-piperazinyl-1) butyl]-3-methylxanthine; and neutralizing the 7-[4-(4-benzhydryl-piperazinyl-1)butyl]-3-methylxanthine with the organic or inorganic acid to form the salt.

18. A pharmacotherapeutic method for treating an allergic illness in a patient by administering to the patient an antihistamine dosage form, comprising: administering an effective amount of a compound 7-[4-(benzylhydrylpiperazinyl-1)butyl]-3-methylxanthine or a pharmaceutically acceptable salt or hydrate thereof in a dosage form, the antihistaminic dosage form capable of producing an antihistaminic effect in the patient to treat an allergic illness in the patient.

19. The method of claim 18, wherein the dosage form is selected from the group consisting of an oral form, an intravenous form, an eye drop form, and a solid drug dose form.

20. The method according to claim 18, wherein the dosage form is capable of administering between about 1 mg to about 3 mg of the compound 7-[4-(benzylhydrylpiperazinyl-1)butyl]-3-methylxanthine or a pharmaceutically acceptable salt or hydrate thereof to the patient per each kilogram of body weight of the patient.

* * * * *